United States Patent [19]

Imfeld

[11] Patent Number: 4,689,427
[45] Date of Patent: Aug. 25, 1987

[54] HYDROQUINONE DERIVATIVES USEFUL IN THE PRODUCTION OF VITAMIN E

[75] Inventor: Marquard Imfeld, Binningen, Switzerland

[73] Assignee: Hoffmann-La Roche Inc., Nutley, N.J.

[21] Appl. No.: 798,510

[22] Filed: Nov. 15, 1985

[30] Foreign Application Priority Data

Nov. 21, 1984 [CH] Switzerland .......................... 5558/84
Sep. 11, 1985 [CH] Switzerland .......................... 3927/85

[51] Int. Cl.$^4$ ...................... C07C 69/00; C07C 37/11
[52] U.S. Cl. ..................................... 560/144; 568/766
[58] Field of Search .......................... 560/144; 568/766

[56] References Cited

FOREIGN PATENT DOCUMENTS 8110299  1/1979  Belgium .
0015562  7/1980  European Pat. Off. ............ 560/144
0036160  11/1983 European Pat. Off. ............ 560/144
2073197  10/1981 United Kingdom ................ 560/144

OTHER PUBLICATIONS

Trost et al., "J. Amer. Chem. Soc.", vol. 103, pp. 5964–5972, (1981).
Tokube et al., "Chemical Letters, Jap. Chem. Soc.", (1985), pp. 561–562.

Primary Examiner—Werren B. Lone
Attorney, Agent, or Firm—Jon S. Saxe; George M. Gould; Dennis P. Tramaloni

[57] ABSTRACT

The present invention is directed to novel hydroquinone derivatives which are useful as intermediates for the manufacture of (R,R,R)-α-tocopherol (natural vitamin E) as well as of racemic α-tocopherol. The invention is also directed to a process for the preparation of the hydroquinone derivatives of the invention.

16 Claims, No Drawings

HYDROQUINONE DERIVATIVES USEFUL IN THE PRODUCTION OF VITAMIN E

BACKGROUND OF THE INVENTION

Several processes for the manufacture of natural vitamin E are known. However, many of these processes are of limited interest since they involve lengthy multistep procedures and, thus, are economically unattractive. Accordingly, natural vitamin E has been extracted almost exclusively from nature sources. There accordingly exists a need for commercially feasible, economical processes for the production of natural vitamin E, in good yield and with high optical purity.

SUMMARY OF INVENTION

The present invention is directed to noval hydroquinone derivatives which are useful as intermediates for the manufacture of (R,R,R)-α-tocopherol (natural vitamin E) as well as of racemic α-tocopherol. The invention is also directed to a process for the preparation of the hydroquinone derivatives of the invention.

DETAILED DESCRIPTION OF THE INVENTION

The process of the invention comprises reacting a compound of the general formula:

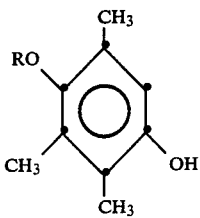

wherein R signifies a hydroxyl protecting group, with 3,4-epoxy-3-methyl-1-butene in the presence of a $d^{10}$-transition metal catalyst to produce a compound of the general formula:

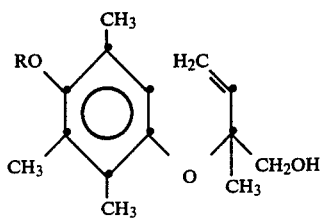

wherein R is as defined in Formula I, followed by Claisen rearrangement of the compound of Formula II to produce, a compound of the general formula:

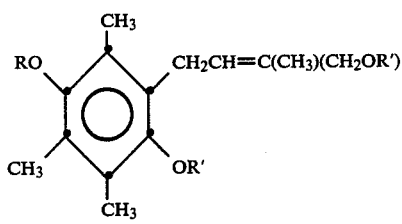

wherein R is as defined in Formula I and wherein R' is hydrogen or an acyl group.

As used herein the term "hydroxyl protecting group" is to be given its commonly understood meaning and refers to a cleavable group which is cleavable by hydrolysis, such as the silyl group, an alkoxymethyl group, e.g. methoxymethyl, the tetrahydropyranyl group or an acyl group, e.g. acetyl, and also a group which is cleavable oxidatively, such as a $C_{1-6}$-alkyl group, e.g. methyl. The preferred hydroxyl protecting group R is acetyl. (See PROTECTIVE GROUPS IN ORGANIC SYNTHESIS, T. W. Greene, John Wiley & Sons, New York, 1981 Chap. 2, pp. 10–86.

The term "acyl group" refers to acyl residues of aliphatic and aromatic carboxylic acids, preferably those containing up to 10 carbon atoms, such as acetyl, propionyl, benzoyl and the like.

Formula III is intended to embrace the cis-isomer (Z-form), the trans-isomer (E-form) as well as mixtures of the cis- and the trans-form.

The term "$d^{10}$-transition metal catalyst" refers to a transition metal complex, the central metal atom of which, has the $d^{10}$-configuration and in which the ligands are uncharged and/or are charged negatively depending on the degree of oxidation of the metal atom. The whole complex is thus uncharged. The central atoms which come into consideration are nickel(O), copper(I), palladium(O), silver(I), platinum(O) and gold(I) (see J. P. Collman and L. S. Hegedus, "Principles and Applications of Organotransition Metal Chemistry", University Science Books, Mill Valley, Calif. 1980, page 13 et seq). Examples of suitable ligands are triorganophosphines such as triphenylphosphine or trimethylphosphine; carbon monoxide; an aromatic ligand such as benzene; a halide such as the chloride; and a sulphonate such as the trifluoromethanesulphonate. As examples of suitable catalysts there are to be named:

Bis-(triphenylphosphine)-nickel(O)-dicarbonyl (see Merck Index 9, 1327), the copper(I) trifluoromethanesulphonate-benzene complex [see Tetrahedron Letters No. 27, 2529–2532(1973)], tetrakis-(triphenylphosphine)-palladium(O) and the compound of the formula Pd° (diop)₂ in which "diop" is an optically active phosphine ligand, namely (2S,3S)-2,3-isopropylidene-2,3-dihydroxy-1,4-bis-(diphenylphosphino)-butane [(+)-diop] or (2R,3R)-2,3-O-isopropylidene-2,3-dihydroxy-1,4-bis-(diphenylphosphino)-butane [(−)-diop] [see e.g. Tetrahedron 33, 2615–2649 (1977) and Topics in Stereochemistry 10, 175–285 (1978)], (trimethylphosphine)-silver(I) chloride [see e.g. Chem. Ber. 105, 3382–3388 (1972)], tetrakis-(triphenylphosphine)-platinum(O) [see e.g. Inorganic Synthesis 11, 105–108 (1968)] and (triphenylphosphine)-gold(I) chloride [see e.g. Chemistry and Industry 1959, 1628].

The palladium(O) catalyst, can be produced, for example, from a palladium(II) salt in the reaction mixture in situ by reduction, e.g. from palladium(II) acetate in the presence of a reduction agent such as formic acid, hydrazine hydrate, a tertiary amine, e.g. triethylamine, or an aliphatic or cyclic ether, e.g. tetrahydrofuran, and a compound which forms a ligand with palladium(O), e.g. triphenylphosphine.

The preferred $d^{10}$-transition metal catalysts for use herein are the palladium(O)-containing complexes.

The reaction of the compound of formula I with 3,4-epoxy-3-methyl-1-butene is conveniently carried out in an inert diluent, especially an organic solvent such as an aliphatic or cyclic ether, e.g. diethyl ether, diisopropyl ether or tetrahydrofuran; an aromatic hydrocarbon, e.g. benzene, toluene or a xylene; or a halogenated aliphatic hydrocarbon, e.g. methylene chloride or chloroform. In the case of ethers, these often also act as the reduction agent for the conversion of palladium-(II) which is used into palladium(O). Thus, for example, diethyl ether and tetrahydrofuran have proved not only to be suitable solvents but also to be suitable reduction agents in any process in accordance with the invention in which palladium(II) salts are used.

This reaction is generally carried out at temperatures between 0° and 30° C., preferably at room temperature.

The amount of $d^{10}$-transition metal catalyst or palladium(II) salt which is present generally amounts to at least 0.01, particularly 0.05 to 100 mol percent based on the amount of compound of formula I, preferably about 0.3 mol percent.

The optional conversion of the compound of formula II into the compound of formula III can be carried out in general under the conditions of Claisen rearrangements which are known per se. Thus, the rearrangement in accordance with the invention is conveniently carried out in an inert diluent, especially an organic solvent such as an aliphatic or aromatic hydrocarbon, e.g. n-heptane, benzene, toluene or a xylene; a heteroaromatic, e.g. pyridine; a halogenated aliphatic or aromatic hydrocarbon, e.g. methylene chloride, chloroform or chlorobenzene; an aliphatic or cyclic ether, e.g. diethyl ether, tetrahydrofuran or dioxan; an ester, e.g. ethyl acetate; a nitrated solvent, e.g. nitromethane; or a formamide, e.g. dimethylformamide. The reaction temperatures can be varied in a wide range, such as $-10°$ C. to 140° C.

The rearrangement is preferably carried out either at low temperatures, i.e. in the temperature range $-10°$ to $+30°$ C., in which it is conveniently carried out either in the presence of a protonic acid such as acetic acid, hydrochloric acid, trifluoroacetic acid, phosphoric acid or sulphuric acid in the presence of a carboxylic acid anhydride or halide, e.g. acetic anhydride or acetyl chloride, or in the presence of a Lewis acid such as iron(III) chloride or boron trifluoride or a complex of such an acid, e.g. its etherate, or at elevated temperatures, i.e. in the temperature range 80° C. to 140° C., especially at about 100° C. in which case, if desired, it is carried out in the presence of a base such as pyridine, piperidine or dimethylaminopyridine.

The Claisen rearrangement in the presence of a carboxylic acid anhydride or a carboxylic acid halide leads to a compound of formula III in which R' signifies an acyl group. In the remaining cases a compound of formula III in which R' signifies hydrogen is obtained.

As a rule, the product of the rearrangement described above exists in the form of a mixture of the isomeric compounds of the general formulae

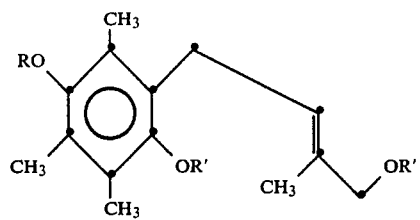

(E-form)

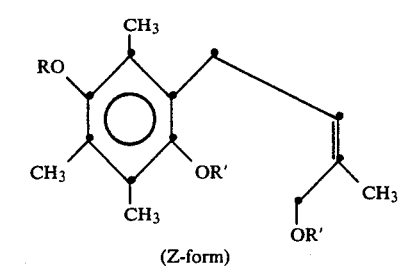

(Z-form)

rather than exclusively in the form of the one or the other isomer. Depending on the reaction conditions of the rearrangement the ratio E-form (IIIa): Z-form (IIIb) amounts to especially from 50:50 to almost 100:0. It has been found, for example, that when the rearrangement is carried out in an acidic medium, e.g. using hydrogen chloride in methylene chloride, the E-form of the product (the trans-isomer) is obtained almost exclusively. On the other hand, in a basic medium, e.g. using dimethylaminopyridine in toluene, the rearrangement yields a substantial amount of the Z-form of the product (the cis-isomer), whereby, however, an increased cis(Z):-trans(E) ratio is favoured by decreasing the amount of base.

The isolation and the purification of the thus-manufactured compounds of formulae II and III can be carried out according to methods known per se. The pure E-form and the pure Z-form of the compound of formula III, i.e. the pure compound of formula IIIa and the pure compound of formula IIIb, can be isolated by methods known per se, e.g. column chromatography.

The compounds of general formulae II, III, IIIa and IIIb are novel and, as indicated above, are likewise objects of the present invention. In these formulae R and R' are preferably acetyl.

The compounds of general formulae III, IIIa and IIIb can be converted into (R,R,R)-α-tocopherol (natural vitamin E), for example in accordance with Reaction Scheme 1 hereinafter. This Reaction Scheme starts from the E-form (compound of formula IIIa), but the reaction steps also apply when the isomer mixture (compounds of formulae IIIa and IIIb) or the Z-form (compound of formula IIIb) is used as the starting material. The process leads in each case to the desired isomer, i.e. to (R,R,R)-α-tocopherol. In this Reaction Scheme the blocked-in wedge-shaped symbols signify that the corresponding residue is situated above the plane of the molecule, while the dotted lines signify that the corresponding residue is situated below the plane of the molecule.

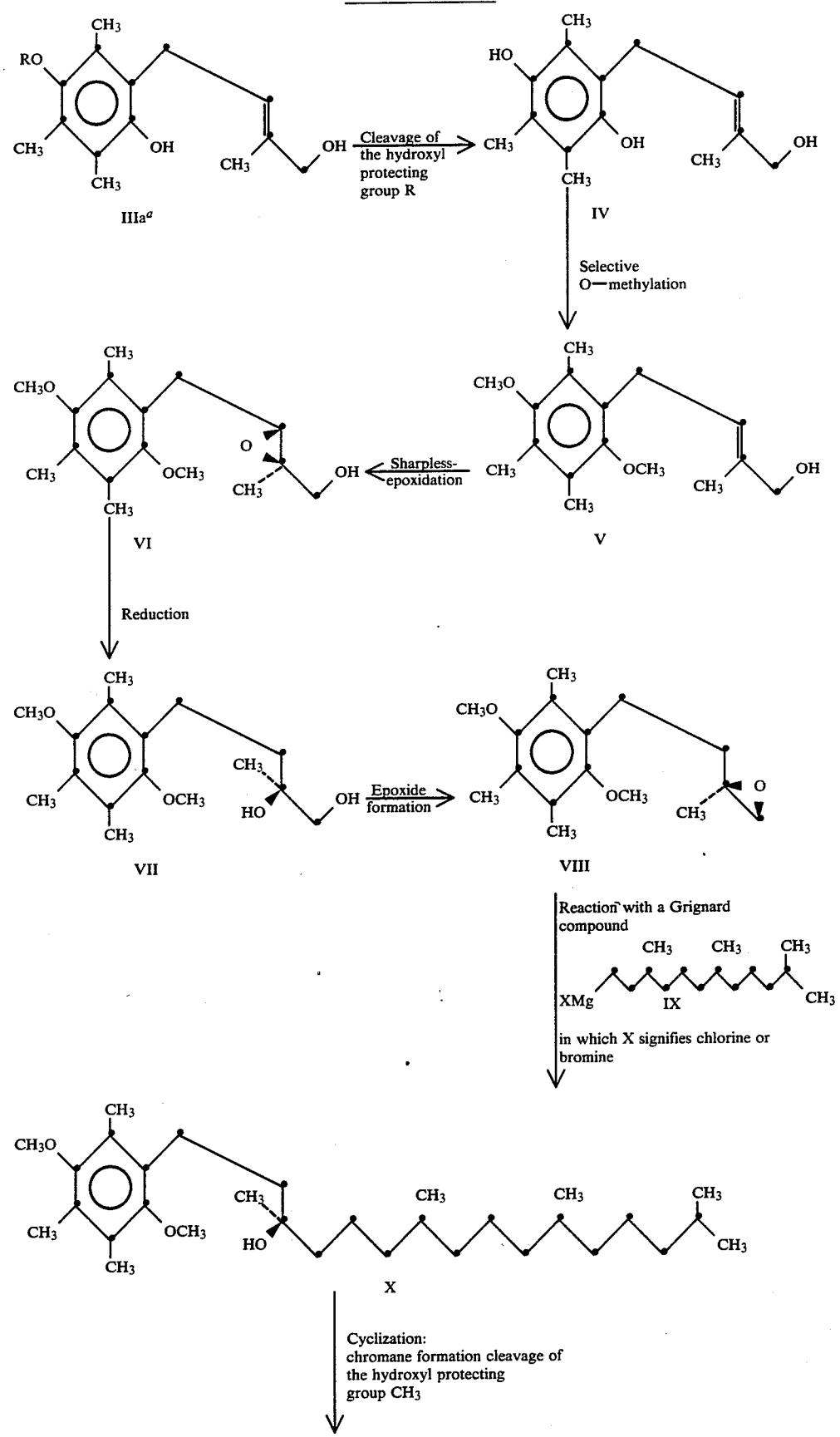
Reaction Scheme 1

Reaction Scheme 1 -continued

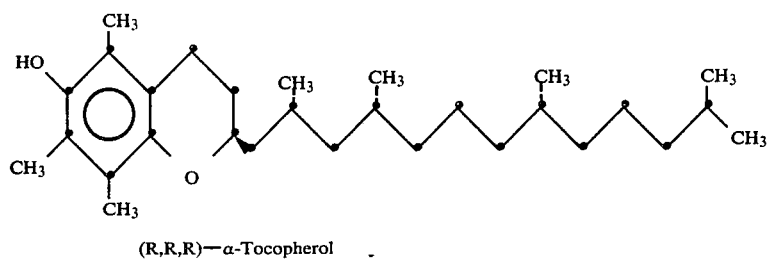

(R,R,R)—α-Tocopherol

XI

The conversion of the compound of formula IIIaa into the compound of formula IV (cleavage of the hydroxyl protecting group R) can be carried out, depending on the nature of the protecting group R, under the reaction conditions relating thereto. Where the protecting group R is cleavable by hydrolysis, this can be carried out in a simple manner, for example by treatment with an acid (R signifies, e.g. silyl, alkoxymethyl or tetrahydropyranyl) or with a base (R signifies e.g. acyl). Where the protecting group R is cleavable oxidatively, the conversion is also carried out in a simple manner, e.g. by treatment with ceric ammonium nitrate [(Ce(NH$_4$)$_2$(NO$_3$)$_6$] and subsequent reductive cyclization of the quinone obtained.

The selective O-methylation of the compound of formula IV to the compound of formula V can also be carried out under reaction conditions which are known per se, e.g. under phase transfer conditions using dimethyl sulphate as the methylating agent, methylene chloride/water as the solvent, a base such as sodium hydroxide or potassium hydroxide and a phase transfer catalyst such as tetrabutylammonium bromide.

The subsequent Sharpless epoxidation of the compound of formula V to the compound of formula VI is a reaction know per se and can be carried out under the usual conditions, e.g. using tert.butyl hydroperoxide as the oxidation agent in the presence of titanium tetraisopropoxide and dibutyl D-tartrate in methylene chloride in the temperature range of −20° C. to room temperature.

The reduction of the compound of formula VI to the compound of formula VII can be carried out using hydrogen in the presence of Raney-nickel or using lithium aluminium hydride. The first-mentioned method is conveniently carried out in an aqueous organic solvent, whereby a water-miscible organic solvent suitably comes into consideration as the organic part of the solvent. Preferred organic solvents are lower alkanols such as methanol, ethanol and propanol; aliphatic or cyclic ethers such as diethyl ether, tetrahydrofuran and dioxan; or ketones such as acetone. Furthermore, the reduction is conveniently carried out in a neutral to weakly alkaline pH range, especially in the pH range of about 7-10, and at temperatures of about 70° C. to about 100° C., preferably at the reflux temperature of the reaction mixture. A solvent mixture having a boiling point as close as possible to 100° C. is especially preferred. The reduction with lithium aluminium hydride is conveniently carried out in an aliphatic or cyclic ether such as diethyl ether, tetrahydrofuran or dioxan and at room temperature.

The conversion of the compound of formula VII into the epoxide of formula VIII can be carried out in a manner known per se. For this purpose, the primary hydroxy group in a compound of formula VII is firstly converted into a leaving group, e.g. into the halide (as the halogen there comes into consideration here chlorine, bromine or iodine) or into a sulphonic acid ester (e.g. tosylate or mesylate) and the like. This conversion can be carried out in a manner known per se. The thus-obtained compound is subsequently treated with a base, also in a manner known per se. As bases there are suitable not only inorganic bases but also organic bases, preferably inorganic bases such as especially sodium hydroxide, potassium hydroxide and the like.

The reaction of an epoxide of formula VIII with a Grignard compound of formula IX can also be carried out in a manner known per se. However, the reaction in the presence of a copper(I or II) catalyst, especially copper(I) n-propylacetylide or a copper(I) halide-dimethyl sulphide complex, is preferred. All solvents which usually come into consideration in the case of Grignard reactions are suitable solvents for this reaction.

The compound of formula X is known and can be converted into (R,R,R)-α-tocopherol (XI) in a known manner. This can be carried out, for example, in a simple manner by treatment with e.g. ceric ammonium nitrate [(Ce(NH$_4$)$_2$(NO$_3$)$_6$] and subsequent reductive cyclization of the quinone obtained.

The compounds of formula III in which R' signifies an acyl group can be reacted further, after the selective cleavage of the acyl group in the side-chain, in an analogous manner to the compound of formula V. The cleavage of the acyl group can be carried out according to methods know per se, for example, in the presence of boron trifluoride, titanium (IV) salts, triethylamine or sodium hydroxide.

The compound of general formula III can, however, also be converted into racemic α-tocopherol, for example in accordance with Reaction Scheme 2 hereinafter.

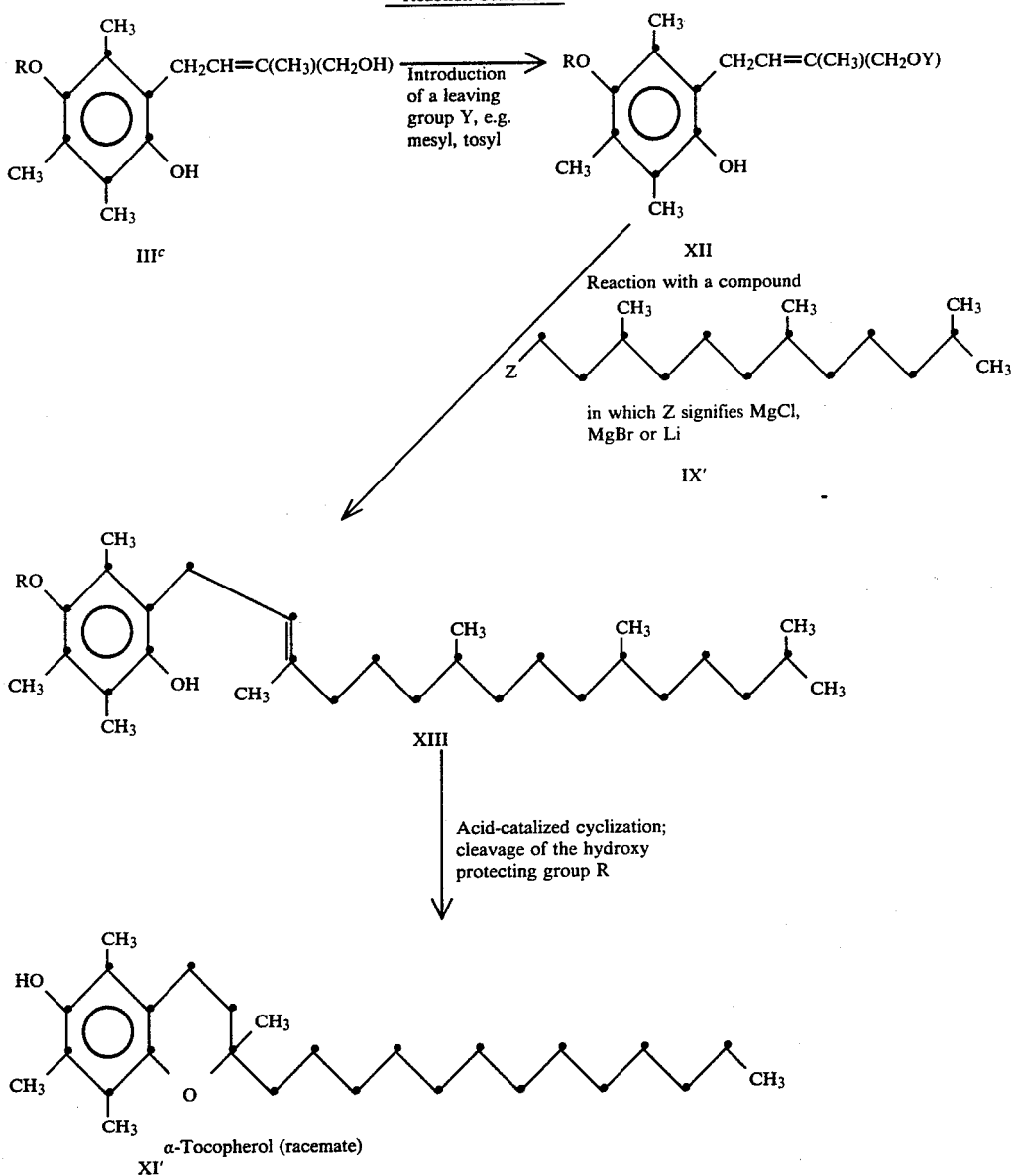

Reaction Scheme 2

The conversion of the compound of formula IIIc into the compound of formula XII (introduction of a leaving group Y) can be carried out, depending on the nature of the leaving group Y, under the known per se reaction conditions relating thereto, e.g. by treating the compound of formula III with methanesulphonyl chloride or p-toluenesulphonyl chloride in pyridine. The subsequent reaction of the compound of formula XII with the compound of formula IX' can also be carried out under reaction conditions known per se. The last reaction step leading to racemic α-tocopherol is conveniently carried out in an organic diluent, preferably toluene, acetic acid, 1,2-dichloroethane or n-heptane, and in the presence of an aqueous mineral acid such as hydrochloric acid or hydrobromic acid and/or in the presence of a Lewis acid such as aluminium trichloride or boron trifluoride.

The isolation and the purification of all reaction products represented in the above Reaction Schemes 1 and 2 can be carried out according to methods known per se.

The process in accordance with the invention is illustrated by Examples 1, 2 and 10 hereinafter, while the stepwise conversion of the product of formula III into (R,R,R)-α-tocopherol is illustrated by Examples 3–9 and 11 hereinafter.

EXAMPLE 1

Preparation of 2,3,6-trimethyl-4-(1'-hydroxymethyl-1'-methyl-allyloxy)-phenyl acetate (a) To a solution of 10 g of 2,3,6-trimethylhydroquinone-1-monoacetate (formula I, R=CH₃CO) in 40 ml of methylene chloride are added at room temperature 120 mg of tetrakis-(triphenylphosphine)-palladium(O) and subsequently 5.0 g of 3,4-epoxy-3-methyl-1-butene. After stirring at room temperature for 30 minutes the reaction mixture is washed with aqueous sodium bicarbonate solution and then the organic phase is dried over anhydrous sodium sulphate and evaporated. From the residue there are obtained by column chromatography (silica gel, diethyl ether/n-hexane) 12 g of pure product, 2,3,6-trimethyl-4-(1'-hydroxymethyl-1'-methyl-allyloxy)-phenyl acetate, in the form of a colourless oil.

(b) The method of (a) is repeated, but with the differences that diethyl ether is used as the solvent and palladium(II) acetate (116 mg) and triphenylphosphine (540 mg) are used in place of tetrakis-(triphenylphosphine)-palladium(O). In this case the palladium(O) catalyst is thus produced in situ. The same product as that of method (a) is obtained.

(c) The method of (a) is repeated, but with the difference that palladium(II) acetate (116 mg), triphenylphosphine (680 mg) and formic acid (50 mg, reduction agent) are used in place of tetrakis-(triphenylphosphine)-palladium(O). In this case the palladium(O) catalyst is thus also produced in situ. The same product as that of method (a) is obtained.

(d) The method of (a) is repeated, but with the differences that the copper(I) trifluoromethanesulphonate-benzene complex (40 mg) is used as the catalyst and the mixture is stirred for 4 hours. The same product as that of method (a) is obtained.

(e) The method of (a) is repeated, but with the differences that bis-(triphenylphosphine)-nickel(O)-dicarbonyl (980 mg) is used as the catalyst and the mixture is heated at reflux temperature for about 16 hours. The same product as that of method (a) is obtained.

(f) The method of (a) is repeated, but with the difference that tetrakis-(triphenylphosphine)-platinum(O) (180 mg) is used as the catalyst. The same product as that of method (a) is obtained.

EXAMPLE 2

Preparation of 4-hydroxy-5-(4'-hydroxy-3'-methyl-2'-butenyl)-2,3,6-trimethyl-phenyl acetate (a) A weak stream of hydrogen chloride is conducted at 0° C. into a solution of 5 g of 2,3,6-trimethyl-4-(1'-hydroxymethyl-1'-methyl-allyloxy)-phenyl acetate in 80 ml of methylene chloride. After stirring at 0° C. for 30 minutes the resulting suspension is poured into aqueous sodium bicarbonate solution. The organic phase is dried over anhydrous sodium sulphate and evaporated, and from the residue (4.9 g) there are obtained by column chromatography (silica gel, diethyl ether/n-hexane) 4.3 g of 4-hydroxy-5-(4'-hydroxy-3'-methyl-2'-butenyl)-2,3,6-trimethyl-phenyl acetate in the E-form, m.p. 144°–146° C.

(b) A solution of 6.3 g of 2,3,6-trimethyl-4-(1'-hydroxymethyl-1'-methyl-allyloxy)-phenyl acetate in 150 ml of toluene is heated at reflux temperature for 6 hours. Thereafter, the reaction mixture is evaporated and the resulting residue is chromatographed (silica gel, diethyl ether/n-hexane/methanol). There are isolated 4.7 g of 4-hydroxy-5-(4'-hydroxy-3'-methyl-2'-butenyl)-2,3,6-trimethyl-phenyl acetate in the E-form, m.p. 144°–146° C., and 0.7 g of the corresponding product in the Z-form, m.p. 138°–139° C.

EXAMPLE 3

Preparation of 4-(2',5'-dihydroxy-3',4',6'-trimethyl-phenyl)-2-methyl-2-butenol 2.9 g of 4-hydroxy-5-(4'-hydroxy-3'-methyl-2'-butenyl)-2,3,6-trimethyl-phenyl acetate are added to a solution of 2.0 g of potassium hydroxide in aqueous ethanol (50 ml of ethanol, 10 ml of water) and the mixture is heated at reflux temperature under argon for 2 hours. Thereafter, the reaction mixture is cooled to room temperature and poured into water. The aqueous mixture is extracted with diethyl ether, and the ether phase is washed in sequence with sodium bicarbonate solution and sodium chloride solution, dried over anhydrous sodium sulphate and evaporated to dryness. The resulting crude product (3.0 g) is recrystallized from methylene chloride. There are obtained 1.32 g of 4-(2',5'-dihydroxy-3',4',6'-trimethylphenyl)-2-methyl-2-butenol in the form of yellow crystals, m.p. 149° C. (with decomposition).

EXAMPLE 4

Preparation of 4-(2',5'-dimethoxy-3',4',6'-trimethylphenyl)-2-methyl-2-butenol A mixture of 3.0 g of 4-(2',5'-dihydroxy-3',4',6'-trimethylphenyl)-2-methyl-2-butenol, 40 ml. of methylene chloride, 6 ml of water, 5.6 g of sodium hydroxide, 0.6 g of potassium carbonate, 1.6 g of dimethyl sulphate and 0.25 g of tert.butylammonium bromide is stirred well at 30° C. under argon for 3 hours and thereafter poured into water. The aqueous mixture is extracted with diethyl ether, and the ether phase is washed in sequence with sodium bicarbonate solution and sodium chloride solution, dried over anhydrous sodium sulphate and evaporated to dryness. From the residue (3.7 g) there are obtained by column chromatography (silica gel, diethyl ether/n-hexane) 1.6 g of 4-(2',5'-dimethoxy-3',4',6'-trimethylphenyl)-2-methyl-2-butenol in the form of white crystals, m.p. 87°–88° C.

EXAMPLE 5

Preparation of (2R,3R)-4-(2',5'-dimethoxy-3',4',6'-trimethylphenyl)-2,3-epoxy-2-methylbutanol 0.594 ml of titanium tetraisopropoxide is dissolved in 10 ml of dry methylene chloride. Thereupon, 524 ml of dibutyl D-tartrate are added dropwise at $-20°$ C. and the mixture is left to stand at $-20°$ C. for 10 minutes. 197 mg of 4-(2',5'-dimethoxy-3',4',6'-trimethylphenyl)-2-methyl-2-butenol are then added and subsequently 180 mg of tert.butyl hydroperoxide (80%) are added dropwise (as a solution in 0.5 ml of methylene chloride). The thus-obtained yellow solution is left to stand at $-20°$ C. for 4 to 5 days, then treated with 5 ml of 1N sodium hydroxide solution, left to warm to room temperature and stirred for 1 hour. The phases are then separated, and the aqueous phase is washed twice with methylene chloride. The combined organic phases are subsequently dried over anhydrous sodium sulphate and concentrated. The thus-obtained colourless oil is dissolved in 20 ml of diethyl ether and stirred with 5 ml of 1N sodium hydroxide solution for 1 hour. The phases are again separated, the aqueous phase is washed twice with diethyl ether and the organic phases are dried over anhydrous sodium sulphate and concentrated. There are obtained 188 mg (98%) of (2R,3R)-4-(2',5'-dimethoxy-3',4',6'-trimethylphenyl)-2,3-epoxy-2-methylbutanol, $[\alpha]_D^{20} +18.2°$ (c=2% in $CHCl_3$).

EXAMPLE 6

Preparation of
(S)-4-(2',5'-dimethoxy-3',4',6'-trimethylphenyl)-2-methyl-1,2-butanediol (a) 185 mg of (2R,3R)-4-(2',5'-dimethoxy-3',4',6'-trimethylphenyl)-2,3-epoxy-2-methylbutanol are dissolved in 5 ml of methanol and the solution is subsequently diluted with 5 ml of water. Thereupon, Raney-nickel is added and the mixture is heated at reflux under hydrogen for 2 hours. After the hydrogen uptake has finished the mixture is filtered, the filter residue is washed with methanol and methylene chloride and the combined filtrate and washings are concentrated on a rotary evaporator. Residual water is distilled off azeotropically by the addition of methylene chloride. The oil obtained is recrystallized from n-hexane/diethyl ether and there are obtained 161 mg of 55% (S)-4-(2',5'-dimethoxy-3',4',6'-trimethylphenyl)-2-methyl-1,2-butanediol (48% yield; GC analysis of the acetonide). Data of the pure substance: M.p. 86°–87° C.; $[\alpha]_D^{20}+2.55°$ (c=5.3% in CHCl$_3$).

(b) 1.10 g of (2R,3R)-4-(2',5'-dimethoxy-3',4',6'-trimethylphenyl)-2,3-epoxy-2-methylbutanol are dissolved in 2 ml of pyridine. 0.5 ml of trimethylchlorosilane is then added and the mixture is left to stand at room temperature for 1 hour. Thereupon, sodium bicarbonate solution is added and the mixture is extracted with toluene. The combined organic phases are dried over anhydrous sodium sulphate and concentrated. The thus-obtained (2R,3R)-4-(2',5'-dimethoxy-3',4',6'-trimethylphenyl)-2,3-epoxy-2-methyl-1-(trimethylsilyloxy)-butane is dissolved in 10 ml of diethyl ether, treated with 40 mg of lithium aluminum hydride and stirred at room temperature for 16 hours. Ammonium hydrogen difluoride solution is then added and the mixture is subsequently extracted with ethyl acetate. The combined organic phases are dried over anhydrous sodium sulphate and concentrated, and the residue is dried further in a higher vacuum. There are thus obtained 804 mg (73%) of (S)-4-(2',5'-dimethoxy-3',4',6'-trimethylphenyl)-2-methyl-1,2-butanediol, m.p. 86°–87° C., $[\alpha]_D^{20}+2.53°$ (c=5.3% in CHCl$_3$).

EXAMPLE 7

Preparation of
(S)-4-(2',5'-dimethoxy-3',4',6'-trimethylphenyl)-1,2-epoxy-2-methylbutane 237 mg of tosyl chloride and 350 mg of (S)-4-(2',5'-dimethoxy-3',4',6'-trimethylphenyl)-2-methyl-1,2-butanediol are dissolved in 1 ml of methylene chloride. 0.180 ml of pyridine is then added dropwise at 0° C. and the mixture is left to stand at 0° C. for 1 hour and then at room temperature for 16 hours. Thereupon, 1 g of ice and 0.3 ml of concentrated hydrochloric acid are added. The mixture is then extracted with methylene chloride and the extract is dried and concentrated. There are obtained 511 mg (95%) of (S)-4-(2',5'-dimethoxy-3',4',6'-trimethylphenyl)-2-methyl-1-toluylsulphonyloxy-2-butanol, $[\alpha]_D^{20}+1.2°$ (c=2.6% in CHCl$_3$).

177 mg of (S)-4-(2',5'-dimethoxy-3',4',6'-trimethylphenyl)-2-methyl-1-toluylsulphonyloxy-2-butanol are dissolved in 1 ml of ethanol and treated with 0.3 ml of alcoholic potassium hydroxide solution (1.5N). The mixture is left to stand at room temperature for 10 minutes, 30 ml of methylene chloride are then added and the mixture is dried over anhydrous sodium sulphate and concentrated. There are obtained 105 mg of (S)-4-(2',5'-dimethoxy-3',4',6'-trimethylphenyl)-2-methyl-1,2-epoxy-butane, m.p. 47°–48° C. $[\alpha]_D^{20}+4.91°$ (c=2.2% in CHCl$_3$).

EXAMPLE 8

Preparation of
(3R,7R,11R)-1-(2',5'-dimethoxy-3',4',6'-trimethylphenyl)-3,7,11,15-tetramethyl-hexadecan-3-ol 5.8 mmol of (3R,7R)-3,7,11-trimethyl-dodecyl bromide are heated at reflux for ¼ hour in 20 ml of diethyl ether with etched magnesium. 1 g of (S)-4-(2',5'-dimethoxy-3',4',6'-trimethylphenyl)-2-methyl-1,2-epoxy-butane and 0.9 g of copper(I) 2-propylacetylide (or 1.2 g of copper(I) bromide-dimethyl sulphide complex) are then added at 0° C. The temperature of the reaction mixture is subsequently left to rise to room temperature and the mixture is stirred for about 16 hours. 10 ml of ammonium chloride are then added and the mixture is extracted with diethyl ether. The extract is dried, concentrated and distilled in a bulb-tube (b.p.$_{0.01}$=140° C.). There are obtained 1.28 g (72%) [or 1.41 g (79%)] of (3R,7R,11R)-1-(2',5'-dimethoxy-3',4',6'-trimethylphenyl)-3,7,11,15-tetramethyl-hexadecan-3-ol as a colourless oil, $[\alpha]_D^{20}-0.67°$ (c=0.9% in CHCl$_3$).

$C_{31}H_{56}O_3$ (476.79) Calc.: C=78.09%, H=11.84%. Found: C=77.92%, H=11.88%.

EXAMPLE 9

Preparation of (2R,4'R,8'R)-α-tocopherol 1.38 g of cerium(IV) ammonium nitrate in 5 ml of water are added while stirring to a solution of 530 mg (1.12 mmol) of (3R,7R,11R)-1-(2',5'-dimethoxy-3',4',6'-trimethylphenyl)-3,7,11,15-tetramethylhexadecan-3-ol in 50 ml of acetonitrile and the mixture is stirred at room temperature for 1 hour. The reaction mixture is extracted three times with 20 ml of methylene chloride each time, and the combined organic phases are dried over anhydrous sodium sulphate and evaporated in a rotary evaporator. There are obtained 480 mg of (3'R,7'R,11'R)-2-(3'-hydroxy-3',7',11',15'-tetramethyl-hexadecan-1'-yl)-3,4,5-trimethyl-1,4-benzoquinone.

The product is dissolved in 100 ml of methanol and hydrogenated over 10% palladium/carbon. 0.5 ml of concentrated hydrochloric acid is then added and the mixture is heated to 50° C. for 2 hours. Thereafter, the mixture is neutralized by the addition of solid sodium hydrogen carbonate and subsequently filtered. The filtrate is evaporated and the residue is chromatographed on silica gel with toluene/ethyl acetate (2:1). In this manner there are obtained 375 mg (90%) of (2R,4'R,8'R)-α-tocopherol (natural vitamin E) as a slightly yellowish oil. The enantiomeric purity of the (2R,4'R,8'R)-α-tocopherol obtained in the above manner amounts to 95%.

EXAMPLE 10

Preparation of
(E,Z)-4-(2',5'-diacetoxy-3',4',6'-trimethylphenyl)-2-methyl-2-butenyl acetate 5.0 g of 2,3,6-trimethyl-4-(1'-hydroxymethyl-1'-methyl-allyloxy)-phenyl acetate (prepared according to Example 1) are dissolved in 50 ml of acetic anhydride and treated with 0.1 g of dimethylaminopyridine. After stirring at room temperature for 5 hours the mixture is held at 100° C. for 7 hours, then cooled to room temperature and poured into aqueous sodium bicarbonate solution. The aqueous mixture is extracted with diethyl ether, and the ether phase is washed in sequence with sodium bicarbonate solution and sodium chloride solution, dried over anhydrous sodium sulphate and evaporated to dryness. There are obtained 5.4 g of a crystallizate of 4-(2',5'-diacetoxy-3',4',6'-trimethylphenyl)-2-methyl-2-butenyl acetate which consists to about 70% of the E-isomeric product and to about 30% of the Z-isomeric product. The pure E-isomer (m.p. 128°-130° C.) can be produced by recrystallization from diisopropyl ether.

EXAMPLE 11

Preparation of
(E)-4-(2',5'-diacetoxy-3',4',6'-trimethylphenyl)-2-methyl-2-butenol 5.0 g of (E)-4-(2',5'-diacetoxy-3',4',6'-trimethylphenyl)-2-methyl-2-butenyl acetate are dissolved in 50 ml of methanol and treated with 0.2 g of boron trifluoride etherate. The mixture is boiled at reflux for 4 hours, then cooled to room temperature and poured into aqueous sodium bicarbonate solution. The aqueous solution is extracted with diethyl ether, and the ether phase is washed in sequence with sodium bicarbonate solution and sodium chloride solution, dried over anhydrous sodium sulphate and evaporated to dryness. From the residue (4.6 g) there are obtained by column chromatography (silica gel, diethyl ether/n-hexane/methanol) 4.0 g of (E)-4-(2',5'-diacetoxy-3',4',6'-trimethylphenyl)-2-methyl-2-butenol in the form of white crystals, m.p. 118°-120° C.

This product can be expoxidized in an analogous manner to Example 5 or to Org. Synth. 62, 66 (1984), the epoxide can be reduced in a manner known per se utilizing hydrides (e.g. diborane) with simultaneous cleavage of the ester function and the hydroquinone alcohol obtained can be converted into (2R,4'R,8'R)-α-tocopherol according to known methods.

I claim:

1. A process for the manufacture of a hydroquinone derivative of the general formula:

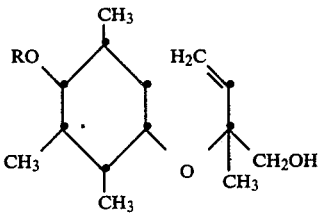

II wherein R is a hydrolytically or oxidatively cleavable hydroxyl protecting group, which comprises reacting a compound of the general formula:

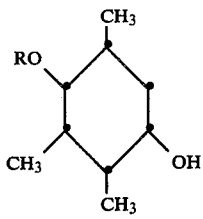

I wherein R is as defined in Formula II, with 3,4-epoxy-3-methyl-1-butene in the presence of a $d^{10}$-transition metal catalyst comprising an uncharged transition metal complex the central atom of which is selected from the group consisting of nickel(O), copper(I), palladium(O), silver(I), platinum(O) and gold(I), and the ligands of which are selected from the group consisting of organophoshines, carbon monoxide, aromatic ligands, halides, sulfonates and combinations thereof.

2. A process according to claim 1, wherein the hydroxyl protecting group R is acetyl.

3. A process according to claim 2, wherein the $d^{10}$-transition metal catalyst is bis-(triphenylphosphine)-nickel(O)-dicarbonyl; the copper(I) trifluoromethanesulphonate-benzene complex; tetrakis-(triphenylphosphine)-palladium(O); the compound of the formula Pd°(diop)$_2$ in which diop is (2S,3S)-2,3-O-isopropylidene-2,3-dihydroxy-1,4-bis-(diphenylphosphino)-butane or (2R,3R)-2,3-O-isopropylidene-2,3-dihydroxy-1,4-bis-(diphenylphosphino)-butane; (trimethylphosphine)-silver(I) chloride; tetrakis-(triphenyphosphine)-platinium(O); or (triphenylphsophine)-gold(I) chloride.

4. A process according to claim 3, wherein the d - transition metal catalyst is a palladium(O)-containing complex.

5. A process according to claim 4, wherein the amount of the $d^{10}$-transition metal catalyst or of a palladium(II) salt producing the palladium(O) catalyst amounts to 0.05 to 100 mol percent based on the amount of compound of general formula I.

6. A process for the manufacture of a hydroquinone derivative of the formula:

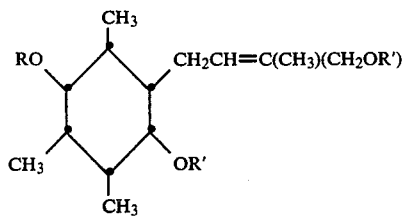

III wherein R is a hydrolytically or oxidatively cleavable hydroxyl protecting group, and R' is hydrogen or an acyl group; which comprises reacting a compound of the formula:

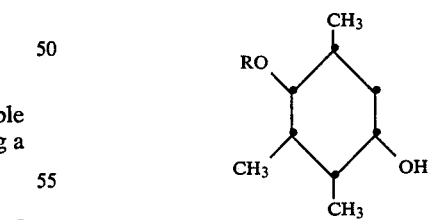

I wherein R is as defined in Formula III, with 3,4-epoxy-3-methyl-1-butene in the presence of a $d^{10}$-transition metal catalyst comprising an uncharged transition metal complex the central atom of which is selected from the group consisting of nickel(O), copper(I), palladium(O), silver(I), platinum(O) and gold(I), and the ligands of which are selected from the group consisting of organophoshines, carbon monoxide, aromatic ligands, halides, sulfonates and combinations thereof to produce a compound of the formula:

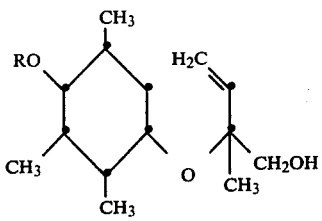

wherein R is as defined in Formula III, and thereafter subjecting the compound of Formula II to a Claisen rearrangement.

7. A process according to claim 6, wherein the hydroxyl protecting group R is acetyl.

8. A process according to claim 7, wherein the $d^{10}$-transition metal catalyst is bis-(triphenylphosphine)-nickel(O)-dicarbonyl; the copper(I) trifluoromethane-sulphonate-benzene complex; tetrakis-(triphenylphosphine)-palladium(O); the compound of the formula Pd°(diop)₂ in which diop is (2S,3S)-2,3-O-isopropylidene-2,3-dihydroxy-1,4-bis-(diphenylphosphino)-butane or (2R,3R)-2,3-O-isopropylidene-2,3-dihydroxy-1,4-bis-(diphenylphosphino)-butane; (trimethylphosphine)-silver(I) chloride; tetrakis-(triphenyphosphine)-platinium(O); or (triphenylphsophine)-gold(I) chloride.

9. A process according to claim 8, wherein the $d^{10}$-transition metal catalyst is a palladium(O)-containing complex.

10. A process according to claim 9, wherein the amount of the d -transition metal catalyst or of a palladium(II) salt producing the palladium(O) catalyst amounts to 0.05 to 100 mol percent based on the amount of compound of general formula I.

11. A compound of the formula:

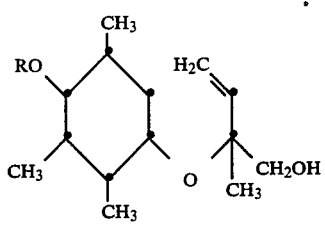

wherein R is a hydrolytically or oxidatively cleavable hydroxyl protecting group.

12. A compound according to claim 11, wherein the hydroxyl protecting group R is acetyl.

13. A compound of the formula

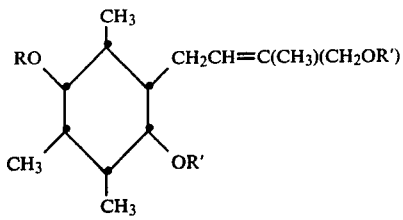

wherein R is a hydrolytically or oxidatively cleavable hydroxyl protecting group, and R¹ is hydrogen or an acyl group, as the isomer mixture or in separated E- or Z-form.

14. A compound according to claim 13, wherein R is acetyl and R' is hydrogen or acetyl.

15. In a process for the preparation of Vitamin E, the improvement comprising reacting a starting material of the formula:

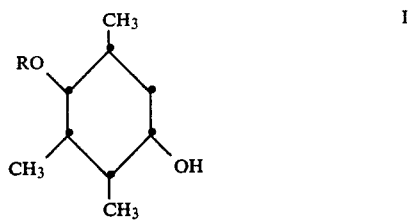

wherein R is a hydrolytically or oxidatively cleavable hydroxyl protecting group, with 3,4-epoxy-3-methyl-1-butene in the presence of a $d^{10}$-transition metal catalyst comprising an uncharged transition metal complex the central atom of which is selected from the group consisting of nickel(O), copper(I), palladium(O), silver(I), platinum(O) and gold(I), and the ligands of which are selected from the group consisting of organophosphines, carbon monoxide, aromatic ligands, halides, sulfonates and combinations thereof to produce a compound of the formula:

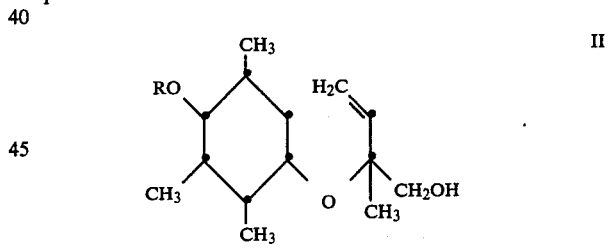

wherein R is as defined in Formula I.

16. The improved process of claim 15 further comprising, subjecting the compound of Formula II to a Claisen rearrangement to produce a compound of the formula:

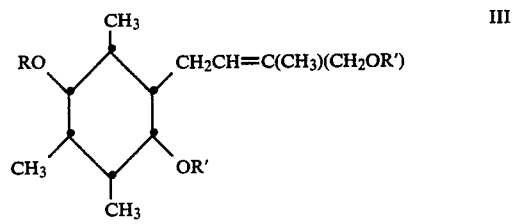

wherein R is the hydrolytically or oxidatively cleavable hydroxyl protecting group and R' is hydrogen or an acyl group.